(12) United States Patent
Ferreira

(10) Patent No.: US 8,622,069 B2
(45) Date of Patent: Jan. 7, 2014

(54) VALVE DEVICE IN A UNIT FOR CONDUCTING A PRODUCT, UNIT OF THIS TYPE AND METHOD FOR OPERATING THE SAME

(75) Inventor: Glenn Ferreira, Aalen (DE)

(73) Assignee: Südmo Holding GmbH (DE)

( * ) Notice: Subject to any disclaimer, the term of this patent is extended or adjusted under 35 U.S.C. 154(b) by 1054 days.

(21) Appl. No.: 12/549,753

(22) Filed: Aug. 28, 2009

(65) Prior Publication Data
US 2010/0108146 A1     May 6, 2010

Related U.S. Application Data

(63) Continuation of application No. PCT/EP2008/001571, filed on Feb. 28, 2008.

(30) Foreign Application Priority Data

Feb. 28, 2007    (DE) .......................... 10 2007 011 084

(51) Int. Cl.
*B08B 3/00*         (2006.01)

(52) U.S. Cl.
USPC ... 137/15.06; 137/240; 137/241; 137/246.11; 137/312; 137/614.11; 137/597

(58) Field of Classification Search
USPC ............. 137/15.01, 15.04, 15.05, 15.06, 238, 137/240, 241, 246.11, 312, 614.11, 597
See application file for complete search history.

(56) References Cited

U.S. PATENT DOCUMENTS 4,344,453 A * 8/1982 Tuchenhagen et al. ....... 137/240
5,232,023 A * 8/1993 Zimmerly .................. 137/637.2
(Continued)

FOREIGN PATENT DOCUMENTS

DE     2430030 A1    1/1976
DE     4243111 A1    6/1994
(Continued)

OTHER PUBLICATIONS

International Preliminary Report on Patentability; PCT/EP2008/001571; Sep. 2, 2009; 6 pages.
(Continued)

*Primary Examiner* — John K Fristoe, Jr.
*Assistant Examiner* — Jessica Cahill
(74) *Attorney, Agent, or Firm* — St. Onge Steward Johnston & Reens LLC

(57) ABSTRACT

A valve device for connecting two conduits in a unit for conducting a product comprises a first shut-off member and a second shut-off member and a first leakage space between the first and the second shut-off members, a first connection for one of the two conduits on a side of the first shut-off member facing away from the leakage space, and a second connection for the other of the two conduits on the side of the second shut-off member facing away from the leakage space. A third shut-off member and a fourth shut-off member and a second leakage space are present between the third and the fourth shut-off members, wherein a central third leakage space is present between the second and the third shut-off members, and wherein the second connection for the other of the two conduits is arranged on a side of the fourth shut-off member facing away from the second leakage space.

22 Claims, 12 Drawing Sheets

(56) References Cited

U.S. PATENT DOCUMENTS

| | | | | |
|---|---|---|---|---|
| 5,275,201 | A | * | 1/1994 | Zimmerly ............... 137/454.6 |
| 5,390,694 | A | * | 2/1995 | Zimmerly et al. ........... 137/240 |
| 5,441,079 | A | * | 8/1995 | Zimmerly ............... 137/637.2 |
| 5,469,880 | A | | 11/1995 | Zimmerly |
| 6,056,003 | A | | 5/2000 | Madsen et al. |
| 6,293,300 | B1 | * | 9/2001 | Dumke et al. ............ 137/312 |
| 7,302,958 | B2 | | 12/2007 | Worczinski |

FOREIGN PATENT DOCUMENTS

| | | |
|---|---|---|
| DE | 10108259 C1 | 1/2002 |
| EP | 0332806 A2 | 9/1989 |
| WO | 9854493 A1 | 12/1998 |

OTHER PUBLICATIONS

International Search Report; PCT/EP2008/001571; Jun. 2, 2008; 3 pages.

* cited by examiner

US 8,622,069 B2

VALVE DEVICE IN A UNIT FOR CONDUCTING A PRODUCT, UNIT OF THIS TYPE AND METHOD FOR OPERATING THE SAME

CROSS-REFERENCE TO RELATED APPLICATIONS

The present application is a continuation of pending International patent application PCT/EP2008/001571 filed on Feb. 28, 2008 which designates the United States, and which claims priority of German patent application No. 10 2007 011 084.9 filed on Feb. 28, 2007.

BACKGROUND OF THE INVENTION

The invention generally relates to valve devices for connecting two conduits in a unit for conducting a product.

The invention also relates to a unit for conducting a product in which at least two conduits are connected to one another via a valve device.

The invention furthermore relates to a method for operating such a unit.

Such a valve device is used in a unit, for example a food processing unit, a pharmaceuticals processing unit or a gene engineering unit, for connecting two conduits to each other in order to reliably separate the processes running in both of the conduits from each other, or else to transfer the process running in the one conduit into the other conduit.

In a food processing unit, a food product, for example milk or a milk product, can flow, for example, in one conduit and a cleaning medium can flow in the other conduit, the cleaning medium being used to clean the other conduit. In the latter case, it is particularly important for the two shut-off members to reliably separate the opposing media flowing in the two conduits from each other because, for example, mixing of the food product flowing in the one conduit with the cleaning medium flowing in the other conduit would spoil the food product.

The leakage space between the two shut-off members serves to make a leakage of one or both shut-off members apparent by the leakage space being monitored with regard to a leakage of medium from one of the two conduits into the leakage space, for example by means of a sensor or simply by visual checking.

The valve device known from DE 42 43 111 A1 is an aseptic double seat valve which ensures that the requirements of reliably separating different processes in the two conduits from each other are met and also satisfies aseptic conditions. Nevertheless, said known valve device has the following disadvantages.

A first disadvantage arises during the cleaning of one of the two shut-off members. For example, when the second shut-off member is cleaned, it is opened such that cleaning medium supplied through the second conduit cleans the second shut-off member and the leakage space. However, it is then not possible, at least under the strict regulations of the Process Milk Ordinance (PMO) standard to allow a product to flow in the first conduit while the second shut-off member is being cleaned. This is because the abovementioned PMO standard requires the presence of a steam barrier between the cleaning process and the product process, at least if the latter is an aseptic product process, said steam barrier additionally separating the product process from the cleaning process. Under these strict regulations, it is therefore compulsory to interrupt the product process in the other conduit for the duration of the cleaning process. This leads to the disadvantage of reduced productivity and economic efficiency of the unit.

A further disadvantage of the known valve device is that an existing unit for conducting a product and having the known valve device can be expanded only with limited functionality. This is explained below with reference to FIGS. 1a) to d).

FIG. 1a) shows a prior art unit for conducting a product 100', which unit is installed, for example, in a food processing factory.

In its starting state as per FIG. 1a), the unit for conducting a product 100' has, for example, a single sterilizer 102'a, an aseptic buffer tank 104'a and a filling group 106'a with two filling stations $F_{11}$ and $F_{12}$. A conduit 108'a leads away from the buffer tank 104'a and is connected to a conduit 110'a, which, in turn, is connected to the sterilizer 102'a, and to a conduit 112'a which leads to the filling group 106'a. At a first junction point 114'a, the conduit 108'a is connected to the conduit 112'a via a known valve device, as described above, and, at a junction point 116'a, the conduit 108'a is likewise connected to the conduit 110'a via a known valve device as described above.

The filling group 106'a is designed, for example, for filling a product into containers made of multi-layered material. The functionality of the unit 100' as per FIG. 1a) consists in the sterilizer 102'a transferring a product via the conduits 110'a, 108'a and 112'a to the filling group 106'a, it being possible for the product to be temporarily stored in the buffer tank 104'a depending on the balance between supply and demand at the filling group 106'a. The known valve devices located at the junctions 114'a, 116'a are appropriately switched for this purpose.

FIG. 1b) now shows the unit 100' as per FIG. 1a) in an expansion stage which would be required, for example, because of increased capacity of the factory in which the unit 100' is being operated.

In said expansion stage, the unit 100' additionally has a second filling group 106'b with which, for example, containers having different volumes than in the filling group 106'a can be filled. In order to increase the buffer capacity, a second buffer tank 104'b has been installed, but the latter is connected via the junction 114'b only to the filling group 106'b, but not to the filling group 106'a. Therefore, the filling group 106'a cannot be supplied with product from the buffer tank 104'b, and the filling group 106'b cannot be supplied with product from the buffer tank 104'a.

FIG. 1c) shows a second expansion of the unit 100' which has become necessary, for example, because the buffer capacity has additionally had to be increased by a third buffer tank 104'c, and, in addition, it has furthermore become necessary to install a second sterilizer 102'b in the factory in which the unit 100' is being operated in order to be able to increase the sterilizing capacity of the unit 100' and/or to be able to use a different type of sterilization. Furthermore, the unit 100' has been expanded by a third filling group 106'c with which, for example, plastic bottles can be filled.

As emerges from FIG. 1c), the buffer tank 104'a continues to be connected only to the filling group 106'a, the buffer tank 104'b only to the filling group 106'b, and the newly added buffer tank 104'c only to the filling group 106'c, and, in addition, the newly added sterilizer 102'b is connected only to the buffer tank 104'c. As emerges from FIG. 1c), supplying of the product via the sterilizer 102'b into the buffer tank 104'a and from there into the filling group 106'b, for example, is not possible, nor are other combinations. The functionality of the unit 100' is therefore increased only to a limited extent by the expansion. Connections are provided only at the junction points shown.

FIG. 1d) finally shows a third expansion of the unit 100' by a fourth buffer tank 104d in order to further increase the buffer capacity of the unit 100'.

In contrast to FIG. 1c), a valve matrix 120' comprising conventional valve devices was additionally installed here between the buffer tanks 104'a to 104'd and the filling groups 106'a-c such that product can be supplied from each buffer tank 104'a to 104'd into each filling group 106'a to 106'c.

However, said valve matrix 120' does not solve the problem of the two sterilizers 102'a and 102'b continuing to be connected only to certain of the buffer tanks 104'a to 104'd, as a result of which the full functionality of the unit 100' continues not to be achieved yet. The productivity of the unit 100' therefore continues to be subject to restrictions because it is not possible, for example, to fill the buffer tanks 104'a and 104'b via the sterilizer 102'b.

On account of the abovementioned disadvantages, there continues to be a demand for a valve device which, firstly, makes it possible to reliably separate processes in the two conduits, which it connects, without, when there is a cleaning process on one side of the valve device, a product process on the other side of the valve device having to be interrupted, and, in particular if an existing unit for conducting a product is expanded, the valve device also permits the greatest possible functionality of the expanded unit without the use of an additional valve matrix.

SUMMARY OF THE INVENTION

Therefore, the invention is based on the object of developing a valve device of the type mentioned at the beginning to the effect that the abovementioned requirements are met.

The invention is furthermore based on the object of providing a unit for conducting a product with such a valve device, and a method for operating such a unit.

According to an aspect of the invention, a valve device for connecting two conduits in the unit for conducting a product is provided, comprising: a first double seat valve having a first shut-off member and a second shut-off member, and a first leakage space between said first and said second shut-off members, a first connection for one of said two conduits on a side of said first shut-off member facing away from said first leakage space, a second double seat valve having a third shut-off member and a fourth shut-off member, and a second leakage space between said third and fourth shut-off members, a second connection for the other of said two conduits on the side of said fourth shut-off member facing away from said second leakage space, said first double seat valve and second double seat valve being arranged head to head with respect to one another, and an intermediate third leakage space arranged between said second shut-off member and said third shut-off member, which is sealed off from said first and second leakage spaces in the closed state of the second and third shut-off member.

The valve device according to the invention therefore has four shut-off members and three leakage spaces between the two conduits, which it connects. The valve device according to the invention therefore corresponds to two conventional valve devices arranged head to head, but, in addition, a further central leakage space is arranged between said two valve devices arranged head to head. If the valve device according to the invention is used in an aseptic unit for conducting a product, an aseptic process in one conduit can therefore be reliably separated, for example, from a cleaning process in the other conduit without the aseptic process having to be interrupted for this purpose. There is therefore even the possibility of, for example, opening the third and fourth shut-off members when the first and second shut-off members are closed and of thoroughly cleaning the third and fourth shut-off members at the same time with a cleaning medium while the first leakage space reliably separates the cleaning process from the process in the first conduit. The same applies to the operation the other way around when the first and second shut-off members are opened in order for them to be cleaned while a product can then be conducted in the second conduit, said product then being reliably separated via the second leakage space from the cleaning process in the first leakage space. In both cases, the third central leakage space in each case permits the thorough cleaning of the first and second or third and fourth shut-off members from all sides because the third central leakage space namely participates in the cleaning process.

In a preferred refinement, at least the first and the second leakage spaces each have a separate steam inlet in order for sterilizing steam to be admitted to the respective leakage space.

In this refinement, the valve device according to the invention even complies with the strict PMO standard which, as explained above, requires a steam barrier to be present between a cleaning process and an aseptic product process. If, for example, the first and second shut-off members are opened for a cleaning process, steam is admitted to the second leakage space between the closed third and fourth shut-off members such that a steam barrier is present between the cleaning process in the first and central third leakage spaces and the conducting of a product in the second conduit. Therefore, even under said strict PMO standard, the conducting of a product in the second conduit advantageously does not have to be interrupted during the cleaning process in the first conduit, the first leakage space and the central third leakage space.

In this case, it is furthermore preferred if the respective steam inlet is respectively provided with a controllable steam inlet valve.

In this connection, it is advantageous that the steam barrier can be controlled and monitored via the control of the respective steam inlet valve.

In both abovementioned refinements, a steam barrier is preferably also assigned to the third central leakage space. Depending on the operating mode, the preferably three steam barriers can be jointly acted upon by steam via the respective controllable steam inlet valve, or steam can also be admitted to only one of the leakage spaces while the other steam inlet valves are closed, and therefore steam is not admitted to the associated leakage spaces.

In a further preferred refinement, a separate outlet leading away downward from the respective leakage space is arranged in each case at least on the first and second leakage spaces.

In this connection, it is advantageous that the sterilizing steam supplied via the respective steam inlet can be removed again through the outlet, but leakage can also be removed from the respective leakage space through the respective outlet, or, as described in more detail below, the respective leakage space can be flooded in a reverse flow through the respective outlet with condensate for cooling the shut-off members in order to avoid an undesirable excessive thermal loading of a product during the subsequent conduction thereof through the respective leakage space.

Also within the scope of the abovementioned refinement, it is preferred if the respective outlet is respectively provided with an outlet valve.

As in the case of the steam inlets, there is therefore the advantage of the respective outlet being controlled and monitored independently of one another.

In a further preferred refinement, the steam inlets are at an angular offset relative to one another that is smaller than approximately 30°, and/or the outlets are at an angular offset relative to one another that is smaller than approximately 30°.

This measure ensures an axially compact configuration of the valve device according to the invention because the angular offset of the steam inlets and/or outlets enables the respective valve control heads to be able to find room next to one another even over a short axial constructional length. In this case, the restriction of the angular offset to a maximum of approximately 30° ensures that, when the valve device according to the invention is fitted in a horizontal position, the outlets enclose an angle of at maximum 15° with respect to the vertical such that the running of, for example, leakage or condensate out of the respective leakage space continues to be ensured.

In a further preferred refinement, the shut-off members and the intermediate third leakage space are arranged in a common, single-piece housing.

This measure likewise advantageously contributes to an axially compact construction because connecting flanges between individual housing sections, which connecting flanges would be required between the first and second leakage spaces in the case of a multi-part configuration of the region of the housing, are avoided.

In this case, it is furthermore preferred if the first connection for the one conduit and/or the second connection for the other conduit lead/leads tangentially on a bottom side into the housing.

If the valve device according to the invention is fitted horizontally, this measure has the advantage that a sump, which would then be difficult to remove because it does not automatically run out of the housing section, cannot form in the housing section into which the respective conduit leads. It is important for there to be complete emptying, in particular if the conduit has been previously cleaned with cleaning medium, since a cleaning medium sump in the housing section may contaminate the product conducted through subsequently.

In a further preferred refinement, the first shut-off member has a first valve disk and a first valve seat, the second shut-off member has a second valve disk and a second valve seat, and the third shut-off member has a third valve disk and a third valve seat, and the fourth shut-off member has a fourth valve disk and a fourth valve seat.

In this refinement, the valve device according to the invention constitutes a twin double seat valve, i.e. two double seat valves are arranged head to head, with a third leakage space additionally being present between the two leakage spaces of the individual double seat valves. In this refinement, the valve device according to the invention is suitable in particular for aseptic units for conducting a product.

In a preferred refinement of the abovementioned development, the first and second valve disks and the third and fourth valve disks are each actuable independently of one another.

This functionality, which is already known in conventional double seat valves, also leads, in the valve device according to the invention, to increased security of the valve device because should, for example, the first valve disk fail, the second can reliably continue to take on the shut-off function.

In a further preferred refinement, the arrangement comprising the first and second shut-off members can be opened and closed independently of the arrangement comprising the third and fourth shut-off members.

This refinement advantageously permits a multiplicity of process functions which will be explained below.

In another preferred refinement, the valve device according to the invention is aseptic.

In this refinement, the valve device according to the invention can advantageously be used in an aseptic unit for conducting a product.

According to another aspect of the invention, a unit for conducting a product is also provided, the unit comprising at least two conduits which are connected via a valve device according to the invention.

The unit preferably has a multiplicity of conduits, of which a first number of conduits are product-supplying and a different number of conduits are product-discharging, wherein each product-supplying conduit is connected to each product-discharging conduit by a valve device according to the invention as per more than one of the abovementioned refinements.

According to still another aspect of the invention, a method for operating a unit for conducting a product is provided, said unit comprising a valve device according to the invention, wherein, in a first operating mode, the first, second, third and fourth shut-off members are opened, and therefore product is transferred from the first conduit through the first, second and third leakage spaces into the second conduit.

In this operating mode, product can therefore be transferred from a product-supplying conduit into a product-removing conduit, the product passing through the three leakage spaces. The product-supplying conduit can come, for example from a sterilizer, and the product-removing conduit can lead, for example, to a filling group.

In the abovementioned first operating mode, it is furthermore preferred if sterilizing steam is present at at least one, preferably at all of the steam inlets of the leakage spaces when the steam inlet valve is closed.

This measure has the advantage that the valve device can be checked for malfunctions of the steam inlet valves by the sterilizing steam which is present but which is not admitted into the leakage spaces. Should sterilizing steam penetrate therein despite the steam inlet valves being closed, this is made noticeable by an increase of the temperature in the discharging conduit in which a corresponding temperature sensor can be provided for monitoring the temperature, or by a drop in pressure in the steam supply line, which can be detected by a corresponding pressure sensor.

In a further preferred refinement of the first operating mode, in order to briefly interrupt the transfer of product from the first conduit into the second conduit, the first, second, third and fourth shut-off members are closed, and then steam is admitted to the first, second and third leakage spaces by opening of at least one of the steam inlet valves.

In this connection, it is advantageous that, during a process-induced interruption to the transfer of product from the first conduit to the second conduit, the remaining product can be removed from the leakage spaces via one outlet, preferably via all of the outlets, after which the leakage spaces can be sterilized by means of sterilizing steam so that, after the interruption, the leakage spaces are again sterile for the subsequent transfer of product.

In a further preferred refinement, in order to interrupt the transfer of product from the first conduit into the second conduit for a longer time, the first, second, third and fourth shut-off members are closed while the first, second and/or third leakage spaces are flooded with sterile condensate through at least one, preferably all of the outlet valves which are opened to the surroundings.

In this connection, it is advantageous if, after the above-described sterilization of the leakage spaces, the latter are cooled via sterile condensate collecting in the leakage spaces such that, during a subsequent continuation of the product flow through the leakage spaces, the product is not subjected to an increased temperature which may damage the product.

In a further preferred refinement, in a second operating mode, when the first and second shut-off members are closed, product flows through the first conduit while, when the third and fourth shut-off members are opened, a cleaning medium is conducted through the second conduit into the second and third leakage spaces, and sterilizing steam is admitted to the first leakage space.

In a third operating mode which is the other way around to the second operating mode, when the third and fourth shut-off members are closed, product flows through the second conduit while, when the first and second shut-off members are opened, a cleaning medium is conducted into the first and third leakage spaces through the first conduit, and sterilizing steam is admitted to the second leakage space.

In these two abovementioned refinements, the one pair of shut-off members assigned to the one conduit can therefore advantageously be thoroughly cleaned by supplying a cleaning medium through said conduit while a product can continue to flow in the other conduit, said product being reliably separated from the cleaning process in the two other facing away leakage spaces by the steam barrier in the facing leakage space.

In a further preferred refinement, in a fourth operating mode, when the first, second, third and fourth shut-off members are closed, steam is admitted to the first, second and/or third leakage spaces.

In this fourth operating mode, the three leakage spaces can advantageously be sterilized when the two conduits are not product-conducting, with it also being possible, as has been described above in the case of a short interruption of a process, for product to flow in the two conduits.

In a further preferred refinement, in a fifth operating mode, when the first, second, third and fourth shut-off members are closed, product flows in one of the two conduits, wherein at least one, preferably all of the steam inlet valves are opened while the first, second and/or third leakage spaces are flooded with sterile condensate through at least one, preferably all of the outlet valves which are opened to the surroundings.

This fifth operating mode in turn advantageously cools the leakage spaces, which have been sterilized beforehand with hot sterilizing steam, and the associated shut-off members.

Further advantages and features emerge from the description below and the attached drawing.

It goes without saying that the features mentioned above and those which have yet to be explained below can be used not only in the respectively stated combination but also in different combinations or on their own without departing from the scope of the present invention.

BRIEF DESCRIPTION OF THE DRAWINGS

Exemplary embodiments of the invention are illustrated in the drawing and are described in more detail hereinafter with respect thereto. In the drawing.

DETAILED DESCRIPTION OF PREFERRED EXEMPLARY EMBODIMENTS

Figure 2:
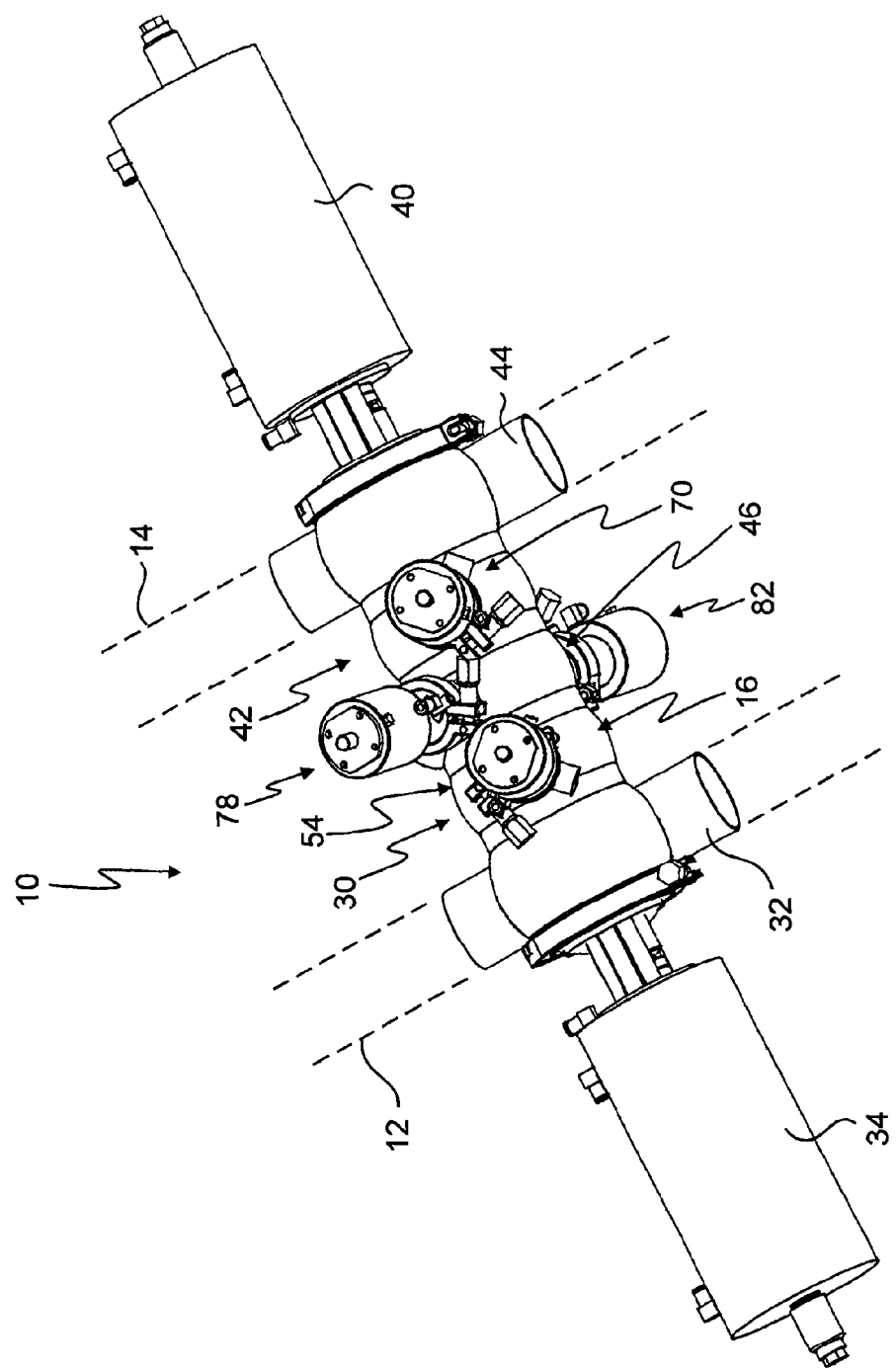
FIG. 2 shows a valve device according to the invention in a perspective illustration.
Figure 3:
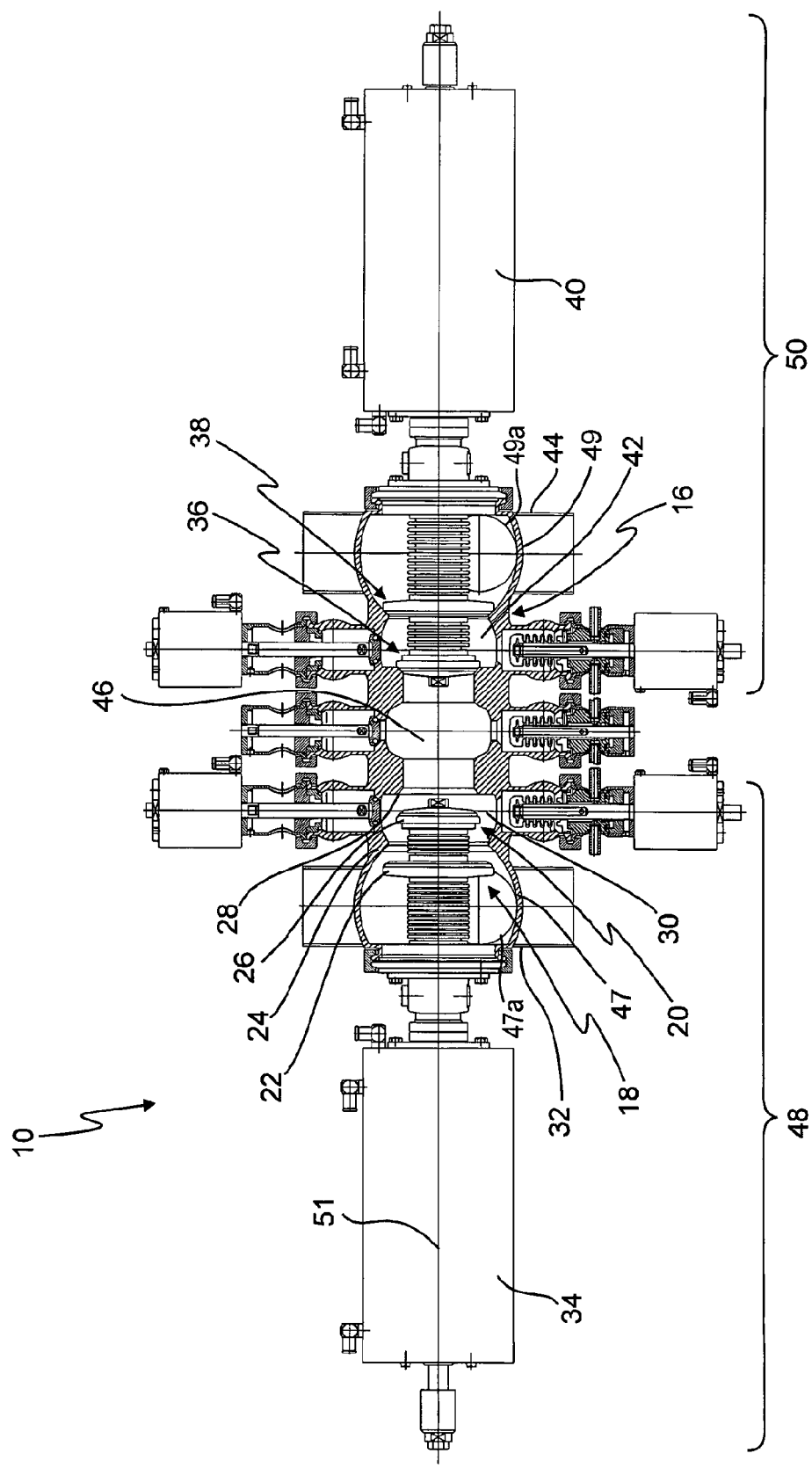
FIG. 3 shows the valve device in FIG. 2 in a side view, partially in longitudinal section.
Figure 3A:
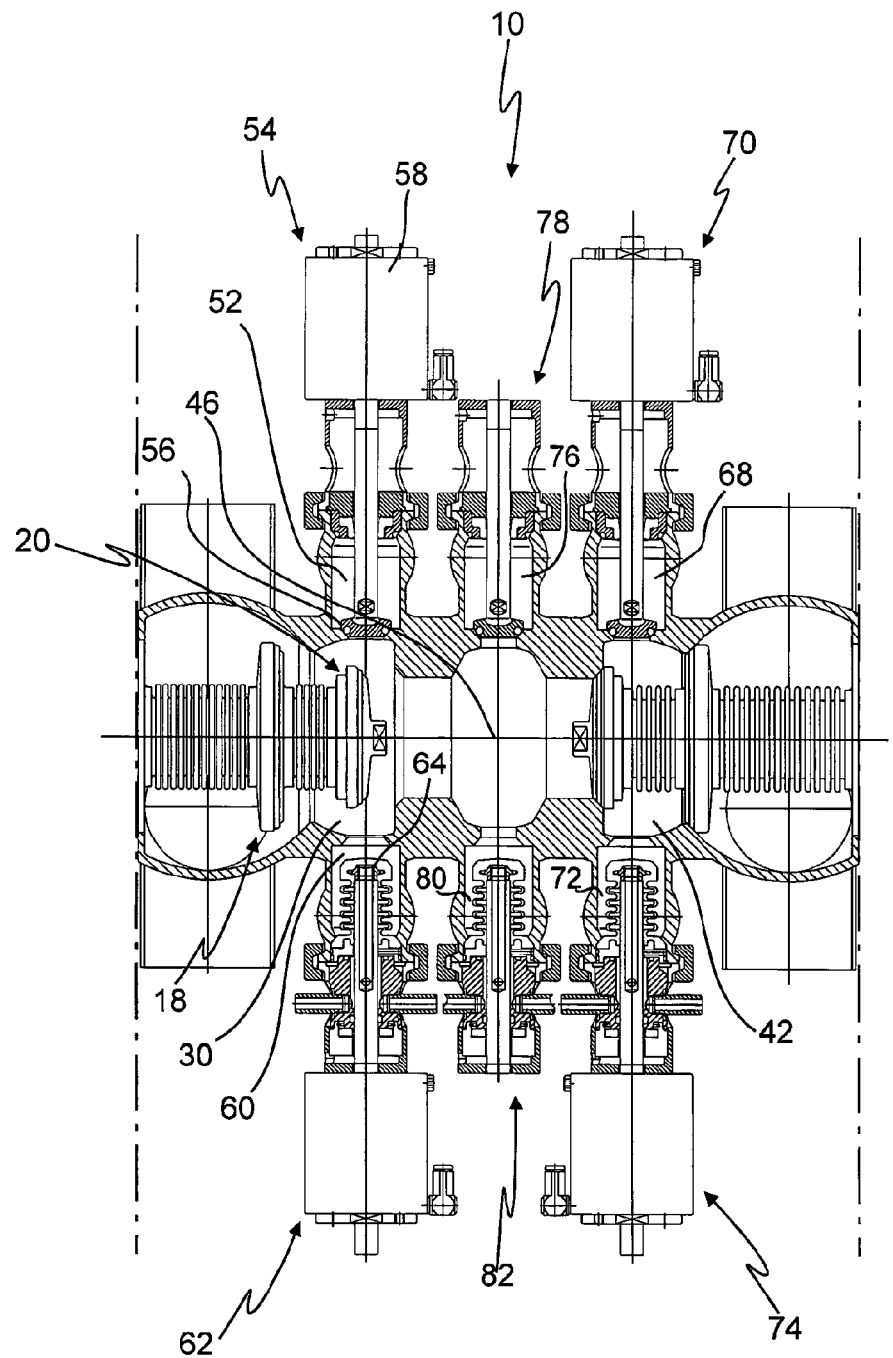
FIG. 3A shows an enlarged cutout of the valve device in FIG. 3.
Figure 4:
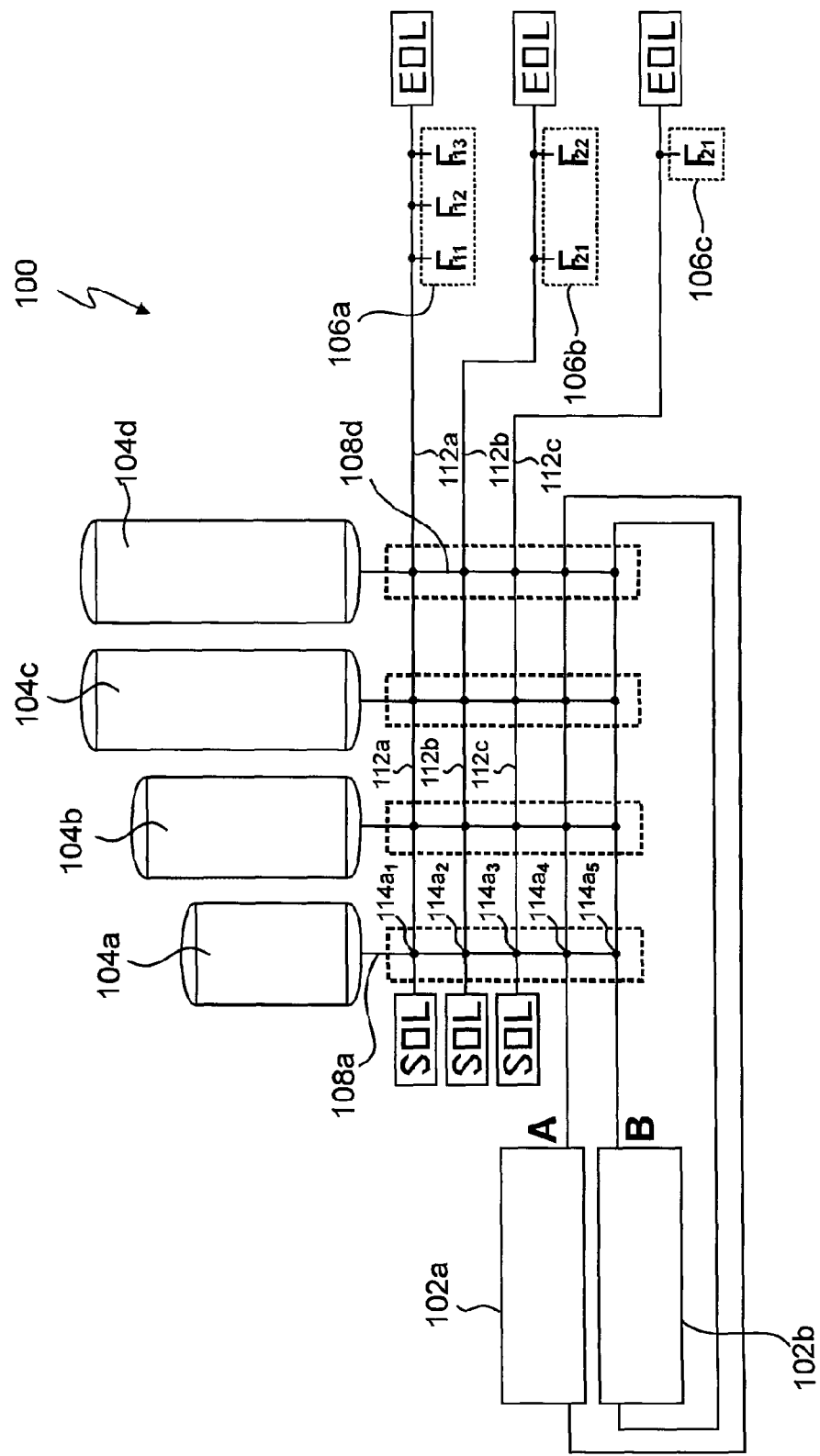
FIG. 4 shows a diagram of a unit according to the invention for conducting a product.

FIGS. 2 and 3, 3A illustrate a valve device which is provided with the general reference number 10 and to which two conduits 12 and 14 of a unit for conducting a product, for example a food processing unit, as illustrated, for example, in FIG. 4, can be connected.

The valve device 10 has a first shut-off member 18 and a second shut-off member 20 in a common, preferably single-piece housing 16.

The first shut-off member 18 has a first valve disk 22 and an associated first valve seat 24 with which the first valve disk 22 comes into contact in a sealing manner in the closed state.

The second shut-off member 20 has a second valve disk 26 and an associated second valve seat 28 with which the second valve disk comes into contact in a sealing manner in the closed state. In FIGS. 3 and 3A, the first shut-off member 18 and the second shut-off member 20 are illustrated in the open position thereof.

A first leakage space 30 is located between the first shut-off member 18 and the second shut-off member 20. In the closed state of the first and second shut-off members 18, 20, the leakage space 30 is sealed off from a first connection 32 for the conduit 12, which connection is located on the side of the first shut-off member 18 facing away from the leakage space 30.

The first valve disk 22 and the second valve disk 26 can be lifted off from their respective valve seat 24, 28 or pressed thereagainst independently of one another by means of a drive 34. The drive 34 is, for example, a pneumatic drive, as illustrated and described in DE 42 43 111 A1, to which reference is made for a detailed description.

Furthermore, a third shut-off member 36 and a fourth shut-off member 38 are arranged in the housing 16, said shut-off members, like the first and the second shut-off members 18, 20, being designed as valve disks with an associated valve seat, and therefore reference can be made to the description above of the first and second shut-off members 18, 20. The third and fourth shut-off members 36, 38 are shown in the closed position thereof. A further drive 40 for actuating the valve disks is provided for the valve disks of the third and fourth shut-off members 36, 38.

A second leakage space 42 is located between the third and fourth shut-off members 36, 38, said leakage space, in the closed state of the third and fourth shut-off members 36, 38, being sealed off from a second connection 44 for the conduit 14, which connection is located on the side of the fourth shut-off member 38 facing away from the first or second leakage space 30, 42.

The third and fourth shut-off members 36, 38 can be opened and closed independently of the first and second shut-off members 18, 20 via the drive 40. The valve disks of the third and fourth shut-off members 36, 38 are additionally actuable independently of each other.

A third central leakage space 46 is located between the second shut-off member 20 and the third shut-off member 36 and is therefore located between the first leakage space 30 and the second leakage space 42. In the closed state of the first, second, third and fourth shut-off members 18, 20, 36, 38, the third leakage space 46 is sealed off from the first leakage space 30 and the second leakage space 42.

In the refinement illustrated, the valve device 10 can also be referred to as a twin double seat valve which is formed from a first double seat valve 48 and a second double seat valve 50 which are arranged head to head with respect to each other and which are connected to each other via the third leakage space 46.

The valve device 10 is in particular aseptic by all of the parts coming into contact with the product being shielded off from the external surroundings, as is known in the case of aseptic valves.

In the refinement shown, the valve device 10 is fitted horizontally, i.e. with its longitudinal axis 51 horizontal. For this purpose, the connections 32 and 44 lead tangentially on a bottom side 47 and 49 into the housing 16, as indicated by circles 47a and 49a.

While, as per FIG. 2, the connections 32 and 44 run parallel to each other, they may also be at an angular offset of, for example, 90° with respect to each other.

Further details of the valve device 10 are described below with respect to FIG. 3A which shows a cutout of the valve device 10 on a larger scale than FIG. 3.

The first leakage space 30 has a steam inlet 52 which can be closed and opened by a controllable steam inlet valve 54. The steam inlet valve 54 has a shut-off member 56 in the form of a valve disk which can be actuated by a drive 58 between a closed position, which is shown in FIG. 3A, and an open position. An outlet 60 which can be opened and closed by an outlet valve 62 faces the steam inlet 52. The outlet valve 62 has a shut-off member 64 in the form of a valve disk which can be lifted off from its corresponding valve seat or can be pressed thereagainst by means of a drive 66.

A pressurized, hot sterilizing steam can be admitted through the steam inlet 52 to the first leakage space 30 while steam, condensate or leakage can be discharged out of the leakage space 30 through the outlet 60. Furthermore, in a certain operating mode, the outlet 60 serves to flood the leakage space 30 with condensate in order to cool the leakage space 30 and the shut-off members 18, 20 therein, as is described further on.

In the same manner, the second leakage space 42 is assigned a steam inlet 68 with a steam inlet valve 70 and an outlet 72 with an outlet valve 74. The third leakage space 46 also has a steam inlet 76 with a steam inlet valve 78 and an outlet 80 with an outlet valve 82, the respective drives of the steam inlet valve 78 and of the outlet valve 82 not being illustrated in FIGS. 3 and 3A but they can be seen in FIG. 2. The steam inlet valves 70, 78 and the outlet valves 74, 82 are designed in the same manner as the steam inlet valve 54 and the outlet valve 62, and therefore reference is made to the above description in this regard.

As revealed in FIG. 2, the steam inlets 52, 68 and 76 and the associated steam inlet valves 54, 70 and 78 thereof are arranged in the circumferential direction relative to one another by an angular offset which is smaller than approximately 30°. If the valve device 10 is fitted in a horizontal position, the steam inlets 52, 68 and 76 are located at the top and are at an angle of approximately 10° to 15° with respect to the vertical. The outlets 60, 72 and 80 and the associated outlet valves 62, 74 and 82 are also offset correspondingly relative to one another, are located at the bottom and, if the valve device 10 is fitted horizontally, form an angle within the range of approximately 10° to 15° with the vertical such that the leakage spaces 30, 42 and 46 can be drained when the outlet valves 62, 74 and 82 are opened.

FIG. 3A shows the outlet valves 62, 74 and 82 in the open position thereof.

As will be described further on, steam barriers can be erected in the first leakage space 30 and in the second leakage space 42, in each case independently of each other, by the introduction of sterilizing steam, said steam barriers reliably separating from one another the process running in the conduit 12 or 14, for example conducting of a product, from the process running in the other conduit 12 or 14, for example a cleaning process, in a manner complying with the requirements of the PMO standard.

FIG. 4 illustrates a unit for conducting a product, which unit is provided with the general reference number 100 and in which at least one, preferably a multiplicity of the valve devices 10 can be used.

Figure 1A:
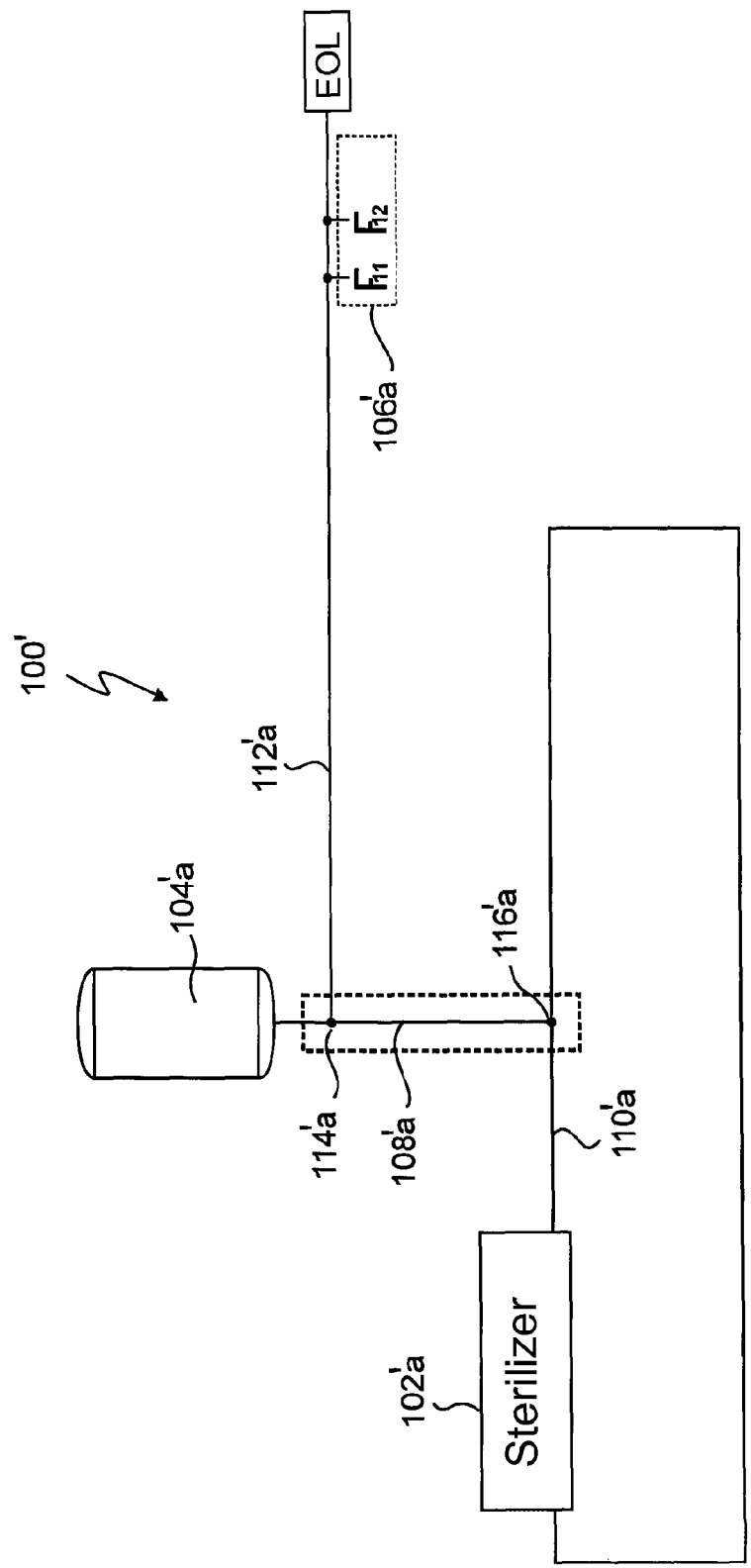
FIGS. 1a) to d) show a diagram of a unit for conducting a product as per the prior art in a basic embodiment (FIG. 1a)) and in three expansion stages (FIG. 1b) to d))
Figure 1B:
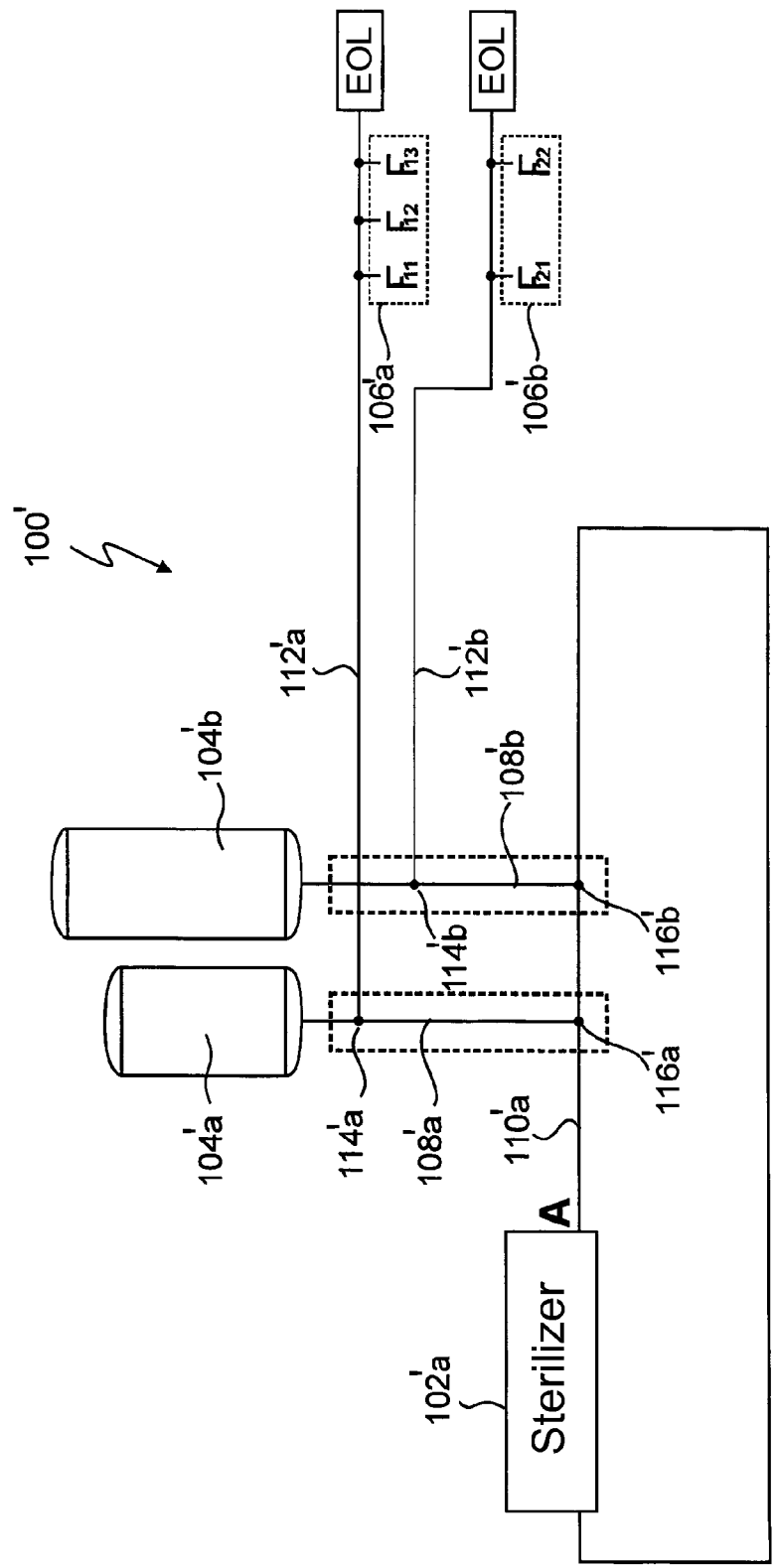
Figure 1C:
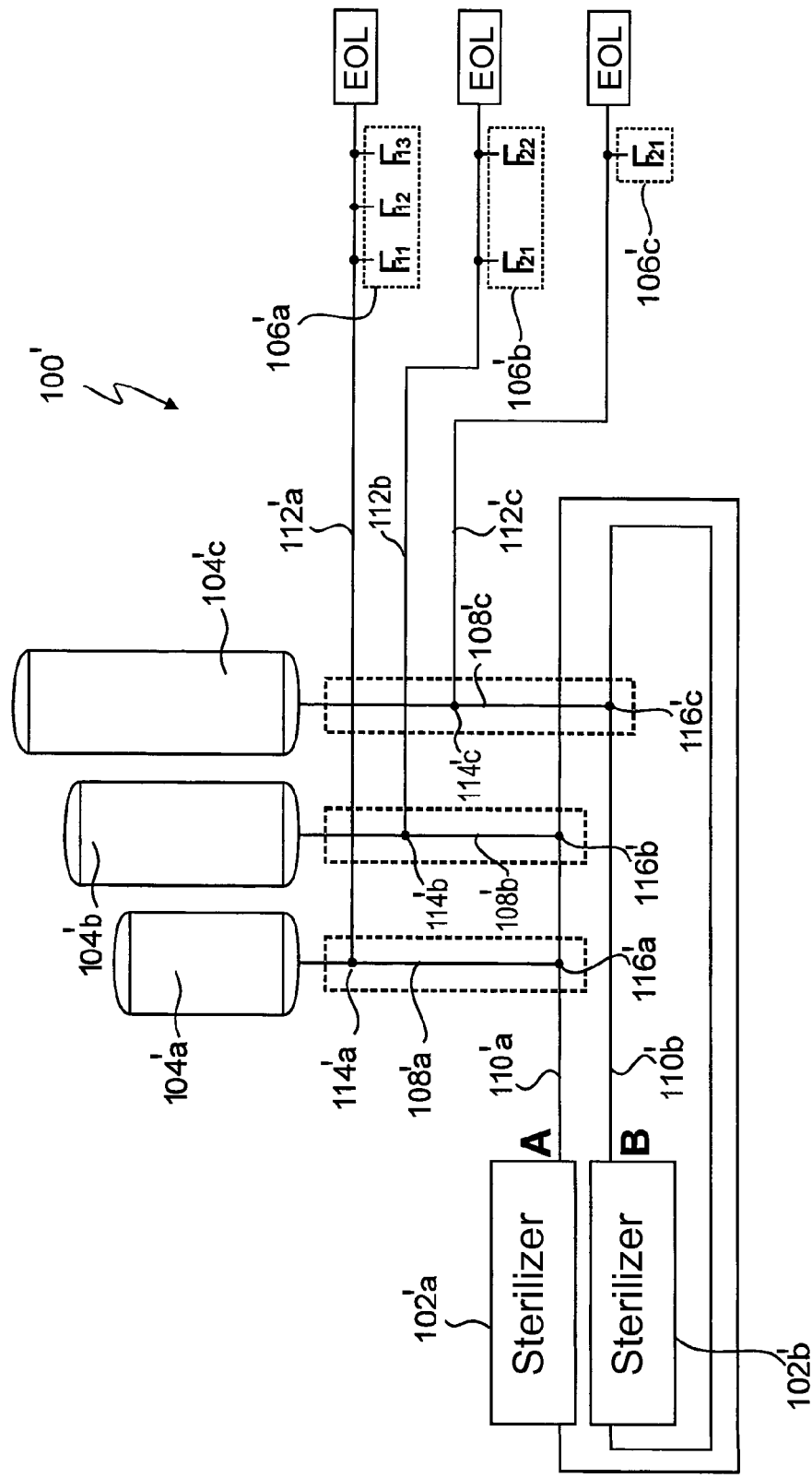
Figure 1D:
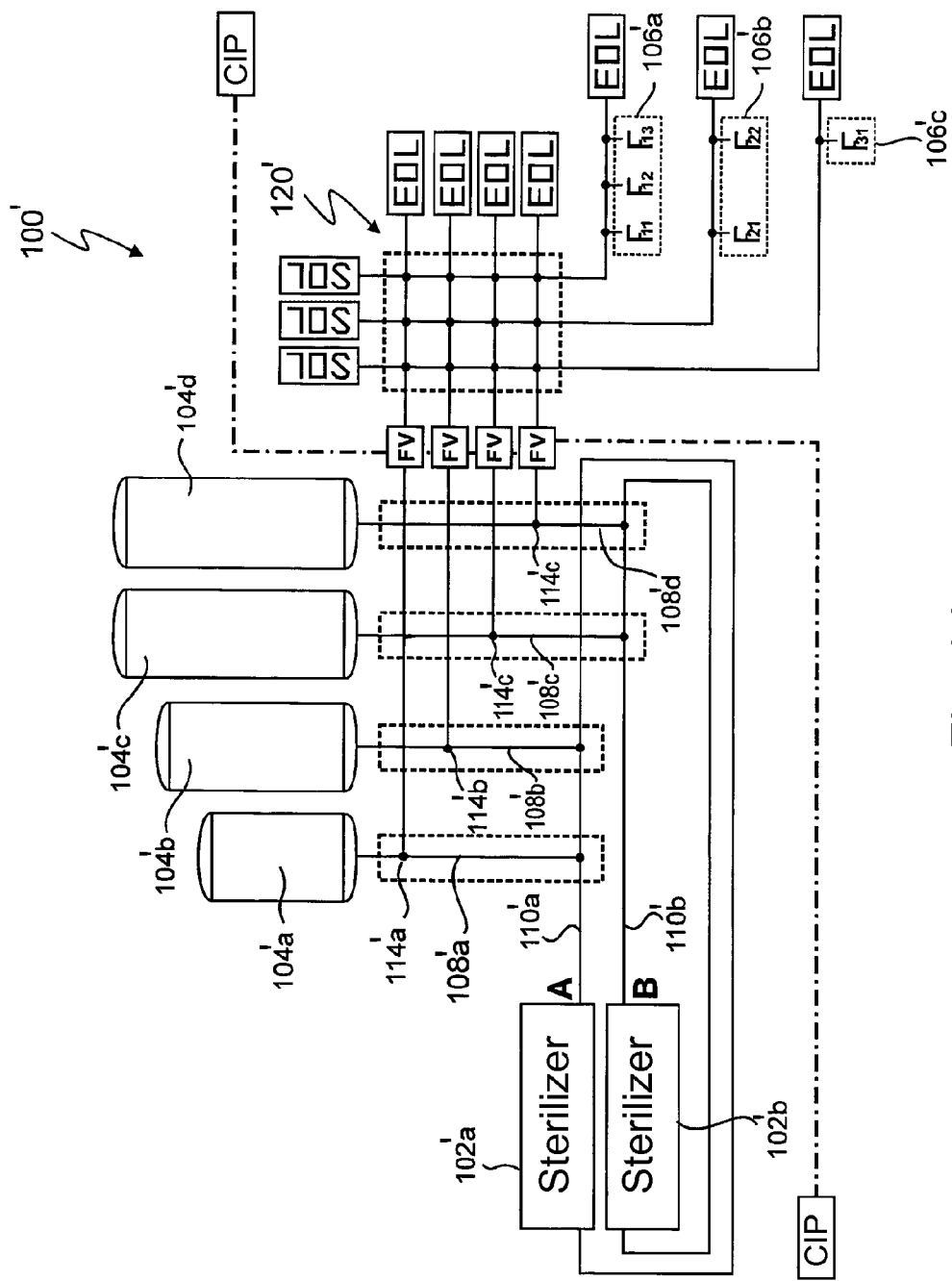

The unit as per FIG. 4 corresponds to the unit 100' in FIG. 1d) which constitutes a unit according to the prior art and has already been described at the beginning.

The unit 100 therefore corresponds to the third expansion stage of the unit 100'. In contrast to the third expansion stage of the unit 100' in FIG. 1d), the functionality of the unit 100 in said third expansion stage is significantly increased over the functionality of the unit 100' as per FIG. 1d). For the unit 100, parts comparable to the unit 100' have used the same reference numbers without a'.

A valve device 10 is located at each of the junction points 114a₁, ..., 114a₅, ..., 114d₁, ..., 114d₅.

In contrast to the unit 100' in FIG. 1d), it is possible, by means of the valve device 10 according to the invention, to connect each product-conducting conduit 108a to 108d to each product-discharging conduit 112a, 112b, 112c and also to connect both sterilizers 102a and 102b to each of the conduits 108a to 108d leading to the buffer tanks 104a to 104d. Another difference over the conventional unit 100' in FIG. 1d) is that the valve matrix 120' is not required, and also the two sterilizers 102a and 102b can now serve to operate each of the buffer tanks 104a to 104d. Similarly, product can be transferred from each of the buffer tanks 104a to 104d to the three filling groups 106a, 106b and 106c.

This greater functionality of the unit 100 is made possible by the configuration of the valve device 10 with four shut-off members and three leakage spaces which can furthermore be used as steam barriers such that processes which must not be mixed can run at the same time in the two conduits which are connected by a valve device 10.

The requirements of reliably separating opposing media in an aseptic process between two conduits which are connected in each case by a valve device 10 at the junction points 114a₁, ..., 114a₅, ..., 114d₁, ..., 114d₅ are always complied with. In this case, shutdown times of the unit 100 are also avoided, since, for example, an aseptic process can run in one conduit or on one side of the valve device while, at the same time, a cleaning process is undertaken in the other conduit or on the other side of the valve device, or different products which must not be mixed can flow on both sides of the valve device 10.

Figure 5:
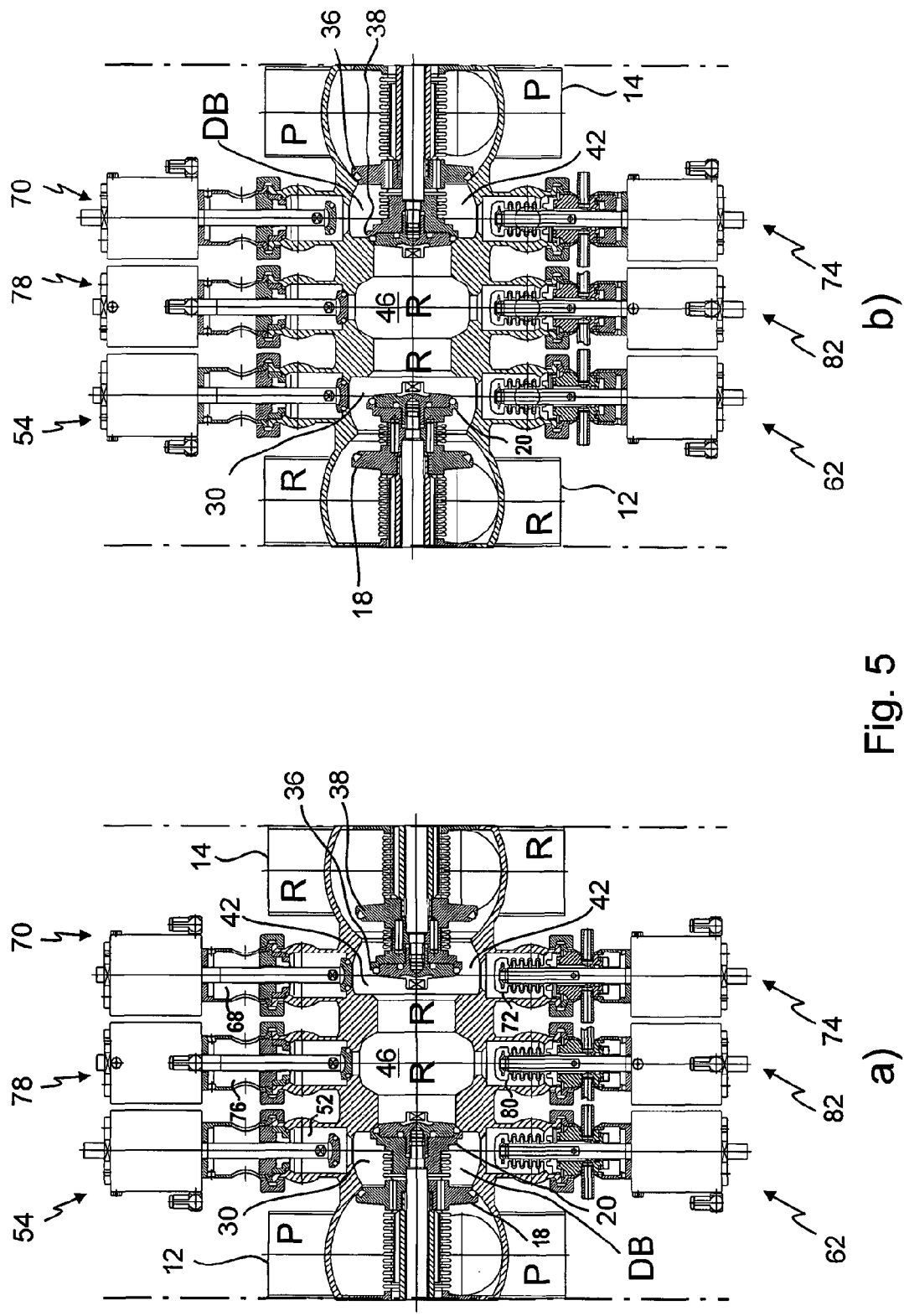
FIGS. 5a) to g) each show a cutout of the valve device in FIG. 2 in various operating modes of the valve device.
Figure 5:
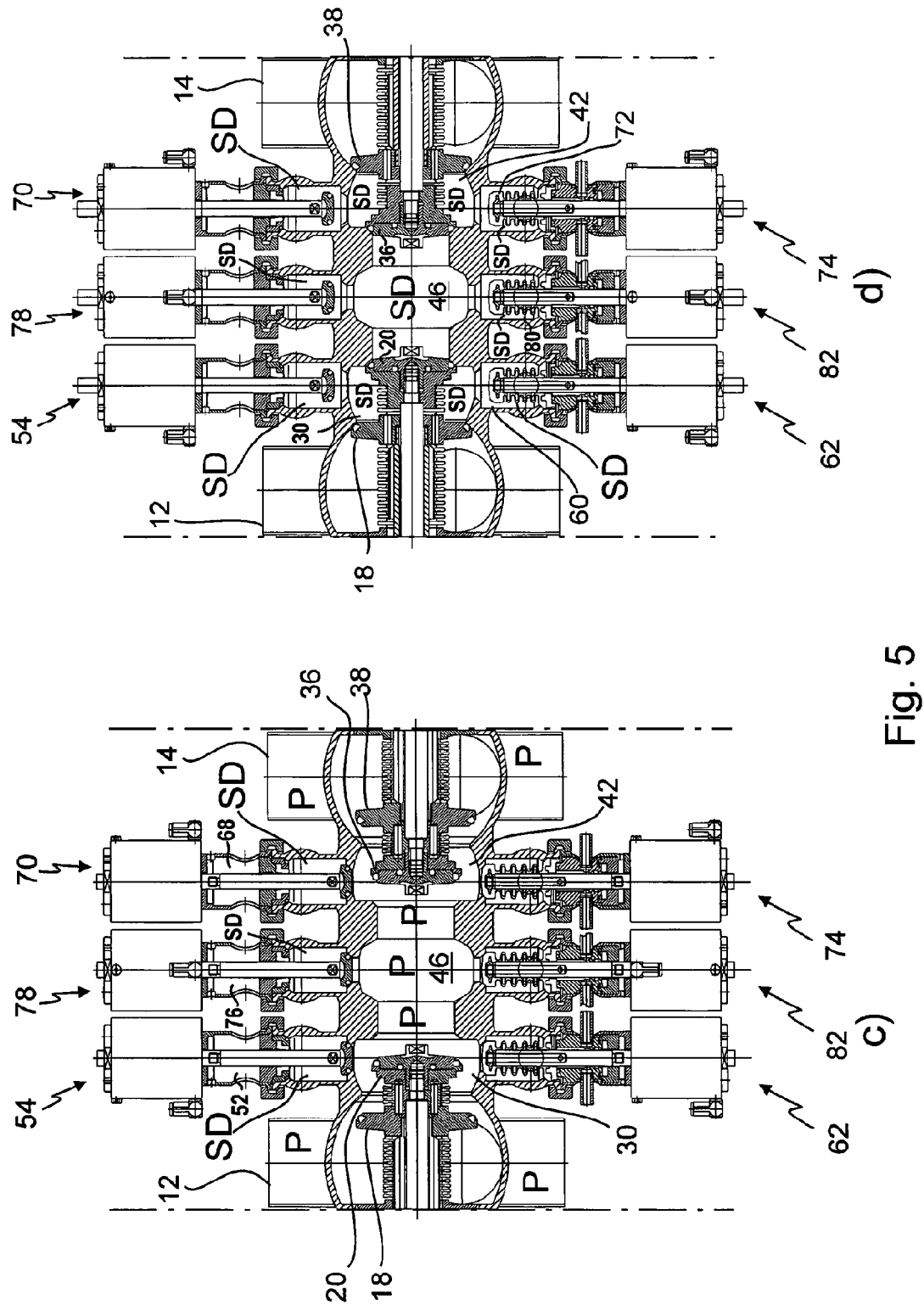
Figure 5:
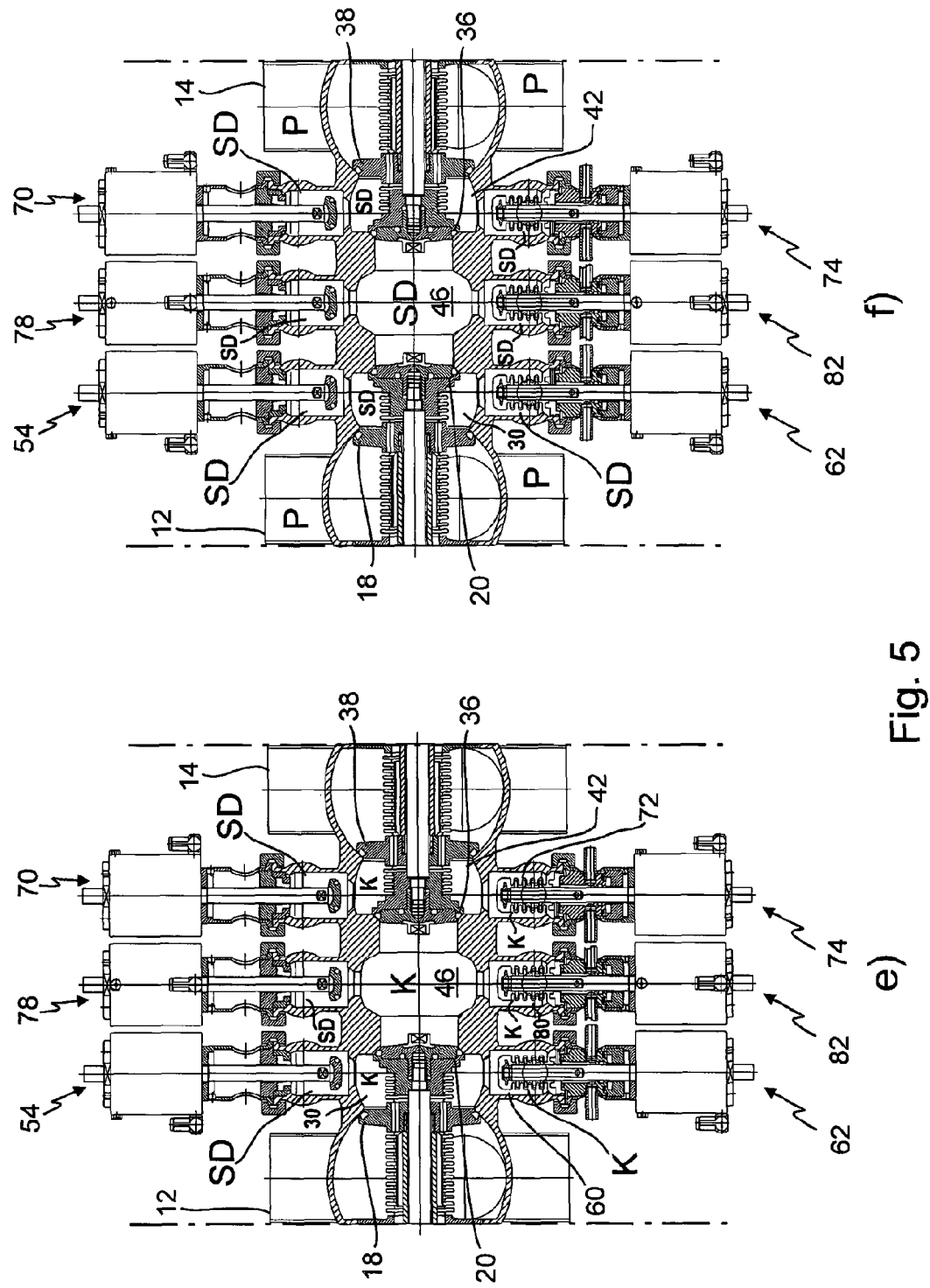
Figure 5:
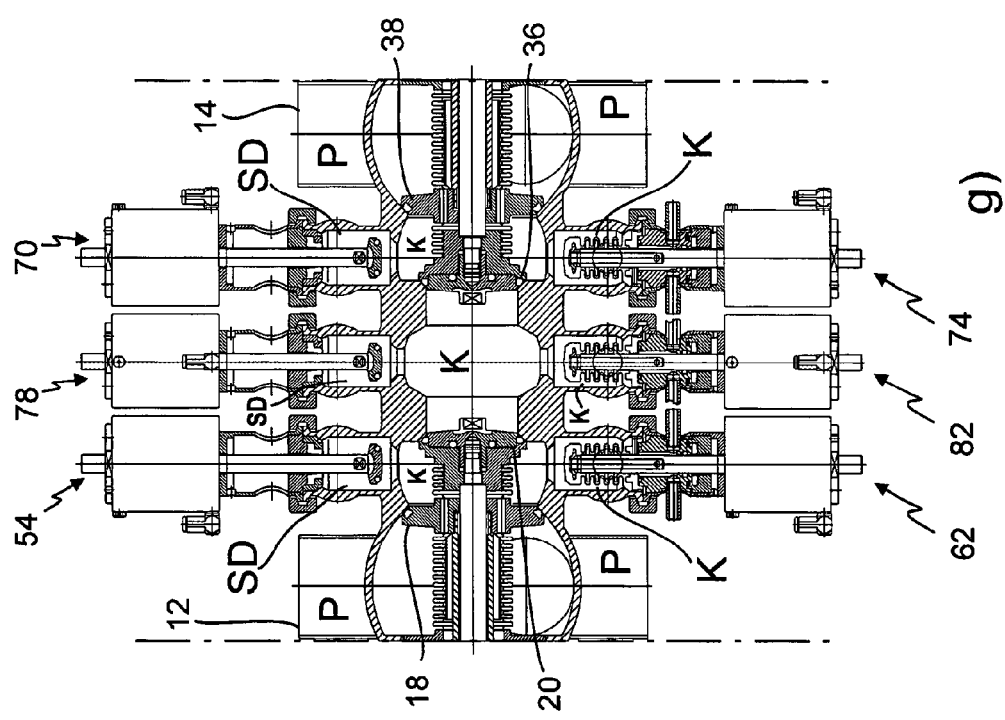

FIGS. 5a) to g) illustrate various operating modes of the unit 100 and of the valve device 10.

FIG. 5a) shows an operating mode in which a product P flows in the conduit 12 and in which the first shut-off member 18 and the second shut-off member 20 are closed. By contrast, the third shut-off member and the fourth shut-off member 36, 38 are open. In this operating mode, cleaning liquid R is supplied to the second leakage space 42 via the conduit 14, the cleaning liquid R also penetrating the third leakage space 46 and thoroughly cleaning the entire region of the third leakage space 46, the second leakage space 42 and the third and fourth shut-off members 36, 38. The presence of the third leakage space 46 enables the cleaning medium R to flood around the third and fourth shut-off members 36, 38 and therefore to thoroughly clean the latter. The cleaning medium R is discharged via the outlets 72 and 80.

During said cleaning process in the third leakage space 46 and the second leakage space 42, sterilizing steam is admitted to the first leakage space 30 through the steam inlet 52 when the steam inlet valve 54 is opened and the outlet valve 62 is opened, the sterilizing steam forming a steam barrier DB between the cleaning process in the second and third leakage spaces 42, 46 and the product P flowing in the conduit 12 such that, during the cleaning process on the side of the valve device 10 on the right in FIG. 5*a*), the conducting of a product on the side of the valve device 10 on the left in FIG. 5*a*) can be continued in the meantime. The steam inlets 68, 76 are closed.

FIG. 5*b*) shows the operating mode which is the other way around to in FIG. 5*a*) and in which a cleaning medium R is introduced into the first and third leakage spaces 30, 46 via the conduit 12 through the opened first and second shut-off members 18, 20 while a product P flows through the conduit 14. The third and fourth shut-off members 36, 38 are correspondingly closed. The steam inlet valve 70 is opened, and the second leakage space 42 is introduced into the second leakage space 42 when the outlet valve 74 is opened in order to separate the cleaning process now taking place on the side of the valve device 10 on the left in FIG. 5*b* from the product process taking place on the side of the valve device 10 on the right in FIG. 5*b*) via a steam barrier DB.

FIG. 5*c*) shows an operating mode in which all four shut-off members 18, 20, 36, 38 are opened such that product P can be transferred from the conduit 12 via the leakage spaces 30, 46, 42 into the conduit 14. In this case, the steam inlet valves 54, 70, 78 are all closed as are all of the outlet valves 62, 74 and 82. However, permanently hot sterilizing steam SD is present under pressure in the steam inlets 52, 68, 76. A loss of pressure in the steam-conducting region would indicate a malfunction of the steam inlet valve or the steam inlet valves 54, 70, 78.

FIG. 5*d*) shows an operating mode in which all four shut-off members 18, 20, 36, 38 are closed and all of the steam inlet valves 54, 70, 78 are opened in order for the three leakage spaces 30, 42 and 46 to be sterilized by means of sterilizing steam. A product may or may also not be flowing in the conduits 12 and 14. The sterilizing steam SD is removed via the outlets 60, 72, 80.

FIG. 5*e*) shows a further operating mode which can follow the operating mode in FIG. 5*d*), i.e. the sterilization of the leakage spaces 30, 42 and 46. In the operating mode illustrated in FIG. 5*e*), following the sterilization as per FIG. 5*d*), that region of the shut-off members 18, 20, 36, 38 which has become hot because of the sterilization, and the leakage spaces 30, 42, 46 are cooled by sterile condensate K, formed by cooling of the sterilizing steam conducted through previously, being introduced to the leakage spaces 30, 42 and 46 via a return through the outlets 60, 72 and 80 when the outlet valves 62, 74, 82 are opened. In the process, the steam inlet valves 54, 70, 78 are opened, but the sterilizing steam is present at a lower pressure, thus favoring the formation of condensate. After all of the steam inlet valves 54, 70, 78 have been closed and after the condensate K is allowed to drain away through the outlets 60, 72 and 80 and after the outlet valves 62, 74, 82 have been closed, then, for example, the operating mode as per FIG. 5*c*) (conducting through of a product) can be begun again.

FIG. 5*f*) shows an operating mode which can follow the operating mode as per FIG. 5*c*). For a brief interruption of the transfer of a product from the conduit 12 to the conduit 14 through the leakage spaces 30, 42, 46, the shut-off members 18, 20, 36, 38 are closed, and sterilizing steam SD is again admitted to the leakage spaces 30, 42 and 46 for the interruption period, as has been described above with respect to FIG. 5*d*).

FIG. 5*g*) illustrates an operating mode during an interruption of the transfer of product from the conduit 12 into the conduit 14 for a longer period of time, the operating mode as per FIG. 5*g*) corresponding to the operating mode in FIG. 5*e*), i.e. sterile condensate for cooling the shut-off members 18, 20, 36, 38 and the leakage spaces 30, 42, 46 is again supplied from below to the leakage spaces 30, 42 and 46.

What is claimed, is:

1. A unit for conducting a product, comprising:
    at least two conduits which are connected to one another via a valve device, said valve device comprising
        a first double seat valve having a first shut-off member and a second shut-off member, and a first leakage space between said first and said second shut-off members,
        a first connection for one of said two conduits on a side of said first shut-off member facing away from said first leakage space,
        a second double seat valve having a third shut-off member and a fourth shut-off member, and a second leakage space between said third and fourth shut-off members,
        a second connection for the other of said two conduits on the side of said fourth shut-off member facing away from said second leakage space,
        said first double seat valve having a first longitudinal axis and said second double seat valve having a second longitudinal axis, said first double seat valve and said second double seat valve being arranged with the first and second longitudinal axes being in alignment with resect to one another, and
    an intermediate third leakage space arranged between said second shut-off member and said third shut-off member, which is sealed off from said first and second leakage spaces in the closed state of the second and third shut-off member.

2. The unit of claim 1, comprising a multiplicity of conduits, of which a first number of conduits are product-supplying and a second number of conduits are product-discharging, and further comprising a multiplicity of said valve devices, wherein each product-supplying conduit is connected to each product-discharging conduit by a respective one of said valve devices.

3. A method for operating a unit for conducting a product, said unit comprising
    at least two conduits which are connected to one another via a valve device, said valve device comprising
        a first double seat valve having a first shut-off member and a second shut-off member, and a first leakage space between said first and said second shut-off members,
        a first connection for one of said two conduits on a side of said first shut-off member facing away from said first leakage space,
        a second double seat valve having a third shut-off member and a fourth shut-off member, and a second leakage space between said third and fourth shut-off members,
        a second connection for the other of said two conduits on the side of said fourth shut-off member facing away from said second leakage space, said first double seat valve having a first longitudinal axis and said second double seat valve ham a second longitudinal axis, said first double seat valve and said second double seat valve being arranged with the first and second longitudinal axes being in alignment with respect to one another, and an intermediate third leakage space arranged between said second shut-off member and said third shut-off member, which is sealed off from said first and second leakage spaces in the closed state of the second and third shut-off member, the method comprising:

opening said first, second, third and fourth shut-off members to transfer a product from the one of said two conduits through the first, second and third leakage spaces into the other of said two conduits.

4. The method of claim 3, wherein at least said first and said second leakage spaces each have a separate steam inlet in order for sterilizing steam to be provided to a respective one of said first and said second leakage spaces, wherein said respective steam inlet is respectively provided with a controllable steam inlet valve, the method comprising providing sterilizing steam to at least one of said steam inlets of said first, second and third leakage spaces while said respective steam inlet valve is closed.

5. The method of claim 3, wherein at least said first and said second leakage spaces each have a separate steam inlet in order for sterilizing steam to be providing to a respective one of said first and said second leakage spaces, the method further comprising, in order to interrupt transfer of product from the one of said two conduits into the other one of said two conduits, closing said first, second, third and fourth shut-off members, and opening at least one of said steam inlet valves to provide sterilizing steam to at least one of said first, second and third leakage spaces.

6. The method of claim 3, wherein a separate outlet leading away downward from said respective first and second leakage spaces is arranged in each case at least on said first and second leakage spaces, the method further comprising, in order to interrupt transfer of product from said one of said two conduits into the other of said two conduits for a longer time, closing said first, second, third and fourth shut-off members, and flooding at least one of said first, second and third leakage spaces with a sterile condensate through at least one of said outlet valves after having been opened.

7. The method of claim 3, further comprising closing said first and second shut-off members so that product flows through said one of said two conduits, opening said third and fourth shut-off members, conducting a cleaning medium through the other of said two conduits into said second and third leakage spaces, and providing sterilizing steam to said first leakage space.

8. The method of claim 3, further comprising closing said third and fourth shut-off members so that product flows through said other of said two conduits, opening said first and second shut-off members, conducting a cleaning medium through said one of said two conduits into said first and third leakage spaces, and providing sterilizing steam to said second leakage space.

9. The method of claim 3, further comprising providing sterilizing steam to at least one of said first, second and third leakage spaces when said first, second, third and fourth shut-off members are dosed.

10. The method of claim 3, wherein at least said first and second leakage spaces each have a separate steam inlet in order for sterilizing steam to be provided to a respective one of said first and said second leakage spaces, and wherein a separate outlet leading away downward from said respective first and second leakage spaces is arranged in each case at least on said first and second leakage spaces, the method comprising closing said first, second, third and fourth shut-off members so that product flows in one of said two conduits, opening at least one of said steam inlet valves and flooding at least one of said first, second and third leakage spaces with sterile condensate through at least one of said outlet valves after having been opened.

11. A valve device for connecting two conduits in a unit for conducting a product, comprising:

a first double seat valve having a first shut-off member and a second shut-off member, and a first leakage space between said first and said second shut-off members, a first connection for one of said two conduits on a side of said first shut-off member facing away from said first leakage space, a second double seat valve having a third shut-off member and a fourth shut-off member, and a second leakage space between said third and fourth shut-off members, a second connection for the other of said two conduits on the side of said fourth shut-off member facing away from said second leakage space, said first double seat valve having a first longitudinal axis and said second double seat valve having a second longitudinal axis, said first double seat valve and said second double seat valve being arranged with the first and second longitudinal axes being in alignment with respect to one another, and an intermediate third leakage space arranged between said second shut-off member and said third shut-off member, which is sealed off from said first and second leakage spaces in the closed state of the second and third shut-off member.

12. The valve device of claim 11, wherein said first and second shut-off members can be opened and closed independently of said third and fourth shut-off members.

13. The valve device of claim 11, wherein said first, second, third and fourth shut-off members and said intermediate third leakage space are arranged in a common, single-piece housing.

14. The valve device of claim 13, wherein at least one of said first connection for said one conduit and said second connection for said other conduit leads tangentially on a bottom side into said housing.

15. The valve device of claim 11, wherein said first shut-off member has a first valve disk and a first valve seat, said second shut-off member has a second valve disk and a second valve seat, and said third shut-off member has a third valve disk and a third valve seat, and said fourth shut-off member has a fourth valve disk and a fourth valve seat.

16. The valve device of claim 15, wherein said first and second valve disks and said third and fourth valve disks are each actuable independently of one another.

17. The valve device of claim 11, wherein at least said first and said second leakage spaces each have a separate steam inlet in order for sterilizing steam to be provided to a respective one of said first and second leakage spaces.

18. The valve device of claim 17, wherein said steam inlets are at an angular offset relative to one another that is smaller than approximately 30°.

19. The valve device of claim 17, wherein said respective steam inlet is respectively provided with a controllable steam inlet valve.

20. The valve device of claim 11, wherein a separate outlet leading away downward from said respective first and second leakage spaces is arranged in each case at least on said first and second leakage spaces.

21. The valve device of claim 20, wherein said outlets are at an angular offset relative to one another that is smaller than approximately 30°.

22. The valve device of claim 20, wherein said respective outlet is respectively provided with an outlet valve.

* * * * *